United States Patent
Raghavendran et al.

(10) Patent No.: US 8,468,239 B2
(45) Date of Patent: Jun. 18, 2013

(54) HEALTH PRESENCE LOCAL MANAGEMENT INTERFACE

(75) Inventors: Vijayakumar Raghavendran, Cary, NC (US); Srikant G. Hemmady, Cupertino, CA (US); Shawn Hsiao-Ping Yang, Morgan Hill, CA (US)

(73) Assignee: Cisco Technology, Inc., San Jose, CA (US)

( * ) Notice: Subject to any disclaimer, the term of this patent is extended or adjusted under 35 U.S.C. 154(b) by 397 days.

(21) Appl. No.: 12/650,300

(22) Filed: Dec. 30, 2009

(65) Prior Publication Data

US 2011/0161475 A1 Jun. 30, 2011

(51) Int. Cl.
*G06F 15/173* (2006.01)

(52) U.S. Cl.
USPC ............. 709/224; 709/220; 709/222; 705/2

(58) Field of Classification Search
USPC ............. 709/222, 224, 230, 227, 208, 216, 709/217, 218, 219, 223; 705/2, 3
See application file for complete search history.

(56) References Cited

U.S. PATENT DOCUMENTS

| | | | | |
|---|---|---|---|---|
| 6,650,944 | B2 * | 11/2003 | Goedeke et al. | 607/60 |
| 7,505,413 | B2 * | 3/2009 | Gous | 370/237 |
| 7,552,101 | B2 | 6/2009 | Bleines | |
| 7,772,965 | B2 | 8/2010 | Farhan et al. | |
| 7,876,687 | B2 * | 1/2011 | Yu | 370/236 |
| 7,970,620 | B2 | 6/2011 | Brown | |
| 8,073,541 | B2 | 12/2011 | Alt et al. | |
| 2003/0025602 | A1 * | 2/2003 | Medema et al. | 340/568.1 |
| 2004/0130446 | A1 | 7/2004 | Chen et al. | |
| 2004/0155772 | A1 * | 8/2004 | Medema et al. | 340/539.12 |
| 2005/0238255 | A1 * | 10/2005 | Niwa et al. | 382/305 |
| 2007/0040889 | A1 * | 2/2007 | Sahashi | 348/14.01 |
| 2007/0073520 | A1 | 3/2007 | Bleines | |
| 2007/0080223 | A1 * | 4/2007 | Japuntich | 235/439 |
| 2007/0156450 | A1 | 7/2007 | Roehm et al. | |
| 2007/0156626 | A1 * | 7/2007 | Roehm et al. | 706/924 |
| 2007/0253021 | A1 * | 11/2007 | Mehta et al. | 358/1.15 |
| 2007/0255115 | A1 * | 11/2007 | Anglin et al. | 600/300 |
| 2007/0299349 | A1 | 12/2007 | Alt et al. | |
| 2008/0004904 | A1 * | 1/2008 | Tran | 705/2 |
| 2008/0146871 | A1 * | 6/2008 | Arneson et al. | 600/101 |
| 2009/0069642 | A1 * | 3/2009 | Gao et al. | 600/300 |
| 2009/0256710 | A1 | 10/2009 | Duckert et al. | |
| 2009/0259720 | A1 * | 10/2009 | Heins et al. | 709/205 |
| 2010/0114514 | A1 * | 5/2010 | Wang et al. | 702/82 |

* cited by examiner

Primary Examiner — Dhairya A Patel
(74) Attorney, Agent, or Firm — Baker Botts L.L.P.

(57) ABSTRACT

In one embodiment, a method includes monitoring a first current status of a communication link coupling a first health-presence unit at a first physical location to a second health-presence unit at a second physical location remote from the first physical location for a remote health-service session. The remote health-service session includes a health-service provider at the second physical location providing a health service to a patient at the first physical location. The method includes monitoring a second current status of the health device of the first health-presence unit and communicating data indicating the first current status and the second current status to the second health-presence unit for presentation to the health-service provider to facilitate assessment by the health-service provider of a usefulness of the health device to the health-service provider during the health-service session in light of the first or second current status.

24 Claims, 4 Drawing Sheets

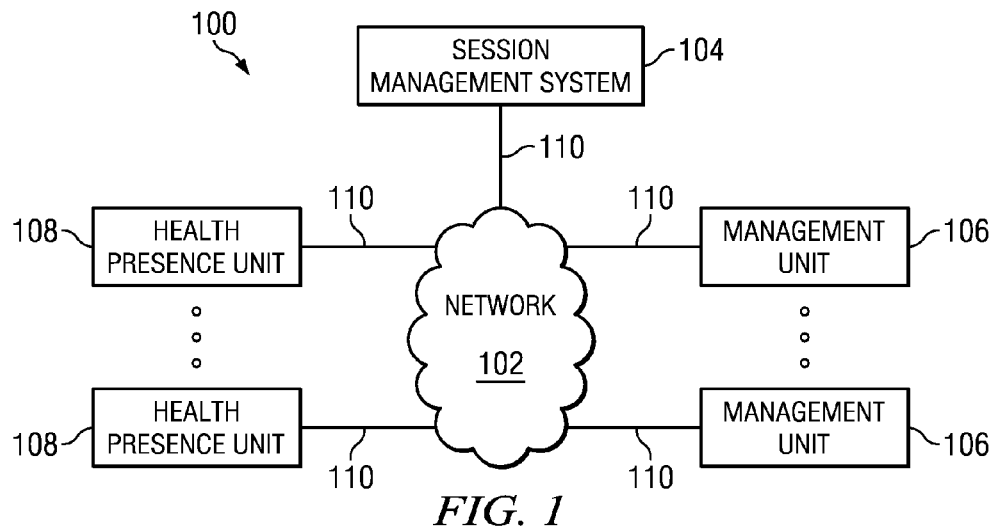
FIG. 1
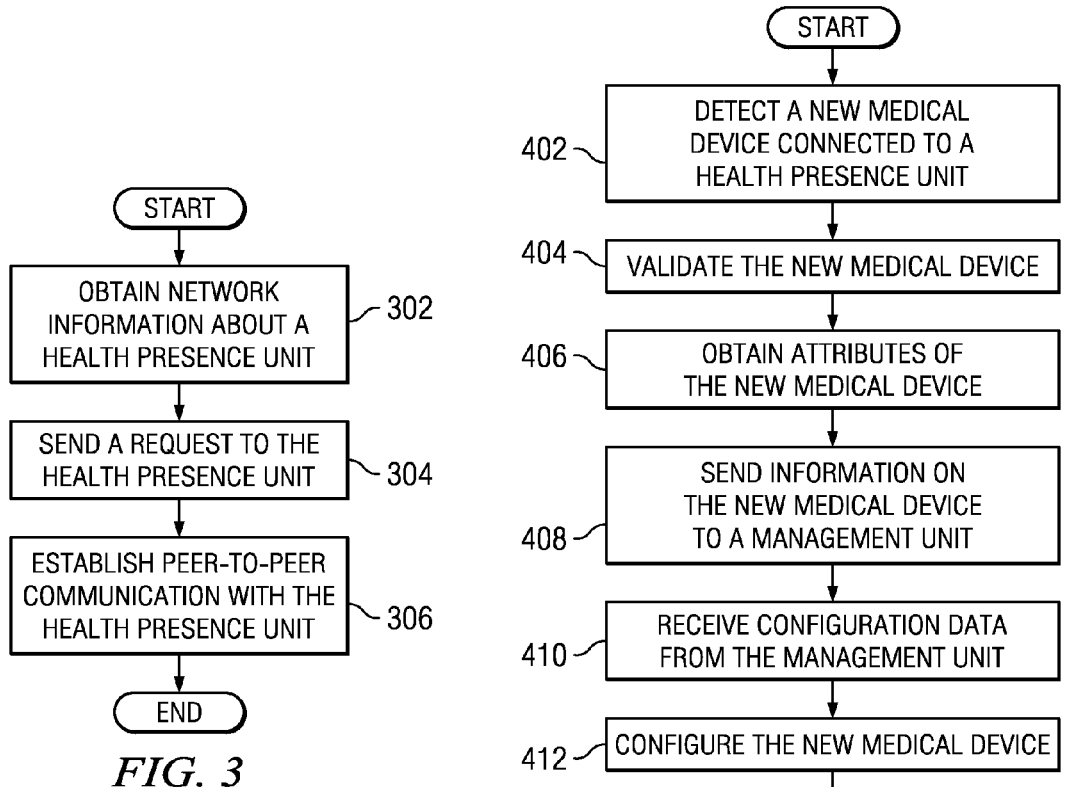
FIG. 3
FIG. 4

HEALTH PRESENCE LOCAL MANAGEMENT INTERFACE

TECHNICAL FIELD

This disclosure relates generally to a health presence system

BACKGROUND

The Internet brings forth numerous benefits, one of which is telepresence. In general, telepresence refers to technologies (e.g., monitors, speakers, cameras, microphones, or computers connected to a network) that enable a person to feel as if he were present, to give the appearance that he were present, or to have the effect that he were present, at a location other than the true location he is at. Telepresence has many practical applications, one of which is in the field of health care. In this case, telepresence, or more specifically, health presence, enables patients and healthcare professionals (e.g., doctors and nurses) at different locations to interact with each other (e.g., to conduct medical sessions or examinations) as if they were at the same location (e.g., in the same room such as a doctor's office).

BRIEF DESCRIPTION OF THE DRAWINGS

FIG. 1 illustrates an example health presence system.
FIG. 3 illustrates an example method for establishing a communication connection between two health-presence units.
FIG. 4 illustrates an example method for connecting a new health device to a health-presence unit.

DESCRIPTION OF EXAMPLE EMBODIMENTS

Overview

Figure 2A:
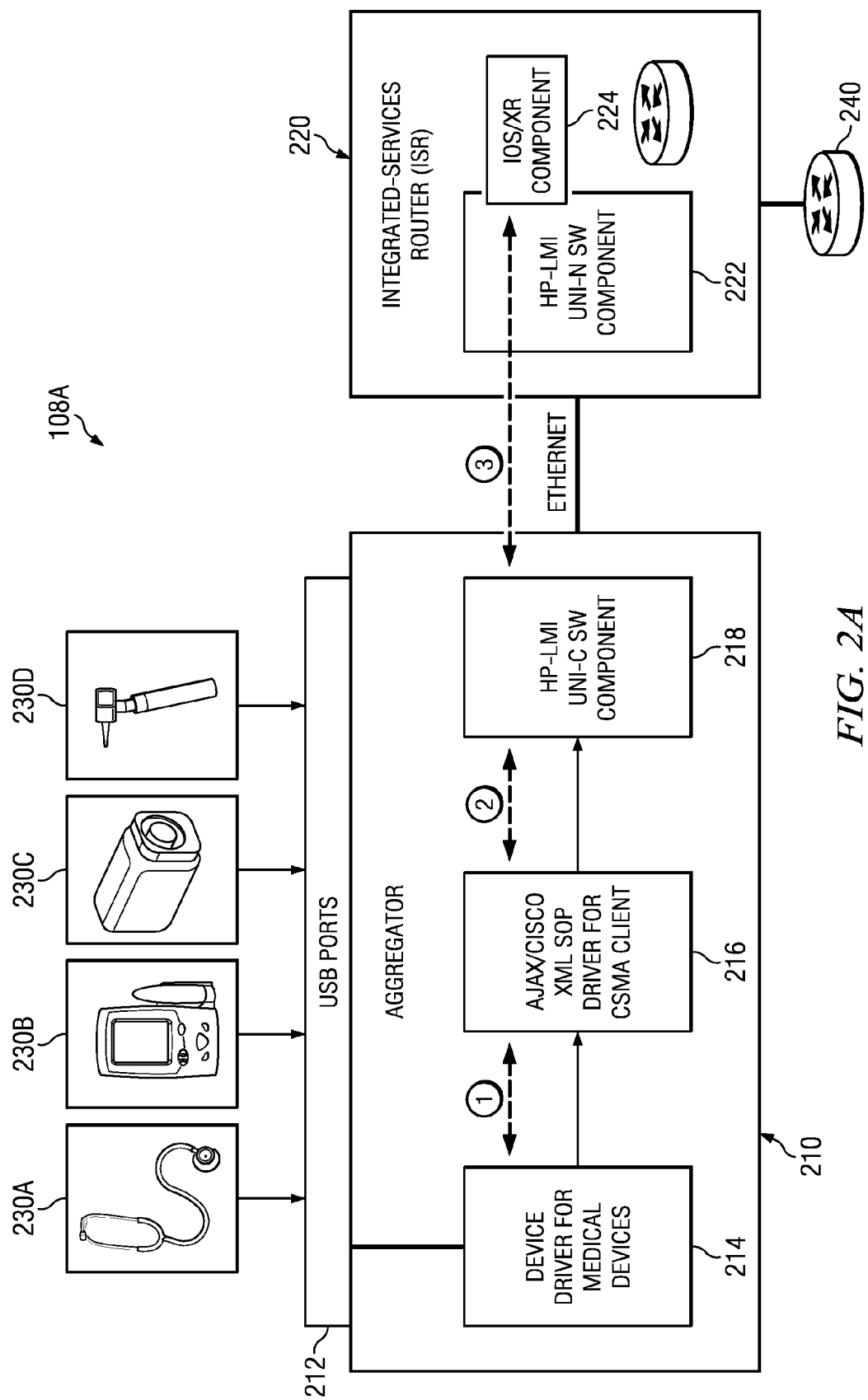
FIGS. 2A and 2B illustrate two example health-presence units.

In one embodiment, a method includes monitoring a first current status of a communication link coupling a first health-presence unit at a first physical location to a second health-presence unit at a second physical location remote from the first physical location for a remote health-service session. The remote health-service session includes a health-service provider at the second physical location providing a health service to a patient at the first physical location. The first current status relates to a current capability of the communication link to communicate commands or data between the first and second health-presence units to support reliable use by the health-service provider of a health device of the first health-presence unit on the patient during the health-service session. The method includes monitoring a second current status of the health device of the first health-presence unit. The second current status relates to a current capability of the health device to be reliably used by the health-service provider on the patient during the health-service session. The method includes communicating data indicating the first current status and the second current status to the second health-presence unit for presentation to the health-service provider to facilitate assessment by the health-service provider of a usefulness of the health device to the health-service provider during the health-service session in light of the first or second current status.

Description

A health presence system developed by CISCO SYSTEMS, INC., called CISCO HEALTHPRESENCE, creates a live "face-to-face visit" experience over the network for healthcare professionals and patients even though they may be hundreds of miles apart. Using market-ready technologies and the network as a platform, CISCO HEALTHPRESENCE combines state-of-the-art video, audio, and medical devices to create an environment similar to which most people experience when they visit their doctors or health specialists. The experience is further enhanced by the availability of medical data (e.g., vital signs or diagnostic information) generated from a variety of medical devices. In short, CISCO HEALTHPRESENCE enables health providers to offer their services over the network and thus to deliver health services to a variety of settings, such as community centers, office buildings, hotels, or educational campuses.

FIG. 1 illustrates an example health presence system 100. Health presence system 100 includes network 102 coupling a session management system 104 (may also be a network directory system), one or more management units 106, and one or more health-presence units 110 to each other. In particular embodiments, network 102 is an intranet, an extranet, a virtual private network (VPN), a local area network (LAN), a wireless LAN (WLAN), a wide area network (WAN), a metropolitan area network (MAN), a portion of the Internet, or another network 102 or a combination of two or more such networks 102. The present disclosure contemplates any suitable network 102.

Links 110 couple session management system 104, management units 106, and health-presence units 108 to network 102. In particular embodiments, one or more links 110 each include one or more wireline, wireless, or optical links. In particular embodiments, one or more links 110 each include any of an intranet, an extranet, a VPN, a LAN, a WLAN, a WAN, a MAN, a portion of the Internet, or another link 110 or a combination of two or more such links 110. In particular embodiments, a link 110 may include one or more links 110. The present disclosure contemplates any suitable links 110.

Session management system 104 may be internal or external to network 102 and may be directly or indirectly coupled to network 102. Session management system 104 may be unitary or distributed across multiple computer systems or datacenters, according to particular needs. The present disclosure contemplates any suitable session management system 104. In particular embodiments, session management system 104 may manage communication sessions between a management unit 106 and a health-presence unit 108, two health-presence units 108, or two management units 106. In particular embodiments, when a first health-presence unit 108 wishes to establish a communication connection with a second health-presence unit 108, the first health-presence unit 108 may obtain network information on the second health-presence unit 108 (e.g., the network address of the second health-presence unit 108) from session management system 104. The first health-presence unit 108 may then use the network information of the second health-presence unit 108 to establish the communication connection with the second health-presence unit 108. In this case, session management system 104 may function as a network directory system. Session management system 104 may provide similar information that enables a health-presence unit 108 to establish a communication connection with a management unit 106 or vice versa. In particular embodiments, session management system 104 may be implemented using Cisco Session Management Application (CSMA).

A management unit 106, also called a management pod 106, may be internal or external to network 102 and may be directly or indirectly coupled to network 102. A management unit 106 may be unitary or distributed across multiple computer systems or datacenters, according to particular needs. The present disclosure contemplates any suitable management units 106. In particular embodiments, a management unit 106 may manage one or more health-presence units 108. In particular embodiments, when a new health-presence unit 108 is added to health presence system 100, a management unit 106 may help configure the components of the new health-presence unit 108 and integrate the new health-presence unit 108 into health presence system 100. In particular embodiments, when a health-presence unit 108 currently connected to health presence system 100 incorporates a new component (e.g., a new health device), a management unit 106 may help configure the new component and integrate the new component into the health-presence unit 108. In particular embodiments, when a health-presence unit 108 currently connected to health presence system 100 experiences functional problems, a management unit 106 may help diagnose the problems or notify a responsible party of the problems.

A health-presence unit 108, also called a health presence pod 108, may be internal or external to network 102 and may be directly or indirectly coupled to network 102. In particular embodiments, a health-presence unit 108 may include one or more health devices 230. A health device 230 may be a system, a device, or a component of a system or device. Health-presence unit 108 may include different types of health devices 230. For example, and not by way of limitation, a health device 230 may include one or more multimedia devices (such as, for example, monitors, speakers, cameras, microphones, or control components), computer systems, medical devices (such as, for example, medical thermometers, stethoscopes, sphygmomanometers, blood-sugar meters, X-ray machines, anesthesia ventilators, apnea monitors, argon enhanced coagulation units, aspirators, auto transfusion units, fetal monitors, electrosurgical units, incubators, infusion pump, pulse oximeters, external pacemakers, ultrasound sensors, electrocardiograph (ECG) units, electroencephalography (EEG) units, phototherapy units, endoscopes, surgical drills and saws, laparoscopic insufflators, phonocardiographs, radiant warmers, zoophagous agents, lytic bacteriophages, breast pumps, surgical microscopes, or ultrasonic nebulizers.), network communication devices (such as, for example, routers), or a combination of two or more such health devices 230. These various types of health devices may each perform different functionalities. For example, a stethoscope may be used to listen to a patient's heart sounds. A pulse oximeter may be used to measure the oxygen saturation of a patient's blood and changes in blood volume in the patient's skin. A sphygmomanometer may be used to measure a patient's blood pressure. Although the present disclosure describes and illustrates particular health devices 230, the present disclosure contemplates any suitable health devices 230.

In particular embodiments, one or more health-presence units 108 may be deployed at different locations accessible to patients and healthcare professionals (e.g., doctors or nurses). For example, a patient at a first health-presence unit 108 and a healthcare professional (e.g., a doctor) at a second health-presence unit 108 may interact with each other via the two health-presence units 108. The two health-presence units 108 may enable the patient and the healthcare professional to experience the same or similar kind of interactions they would experience if they were at the same location.

In particular embodiments, new health-presence units 108 may be added to health presence system 100 (e.g., deployed at new locations) or existing health-presence units 108 may be removed from health presence system 100. In particular embodiments, for a health-presence unit 108 deployed in health presence system 100, new health devices (e.g., new medical devices) may be added to the health-presence unit 108 or existing health devices may be removed from the health-presence unit 108.

Figure 2B:
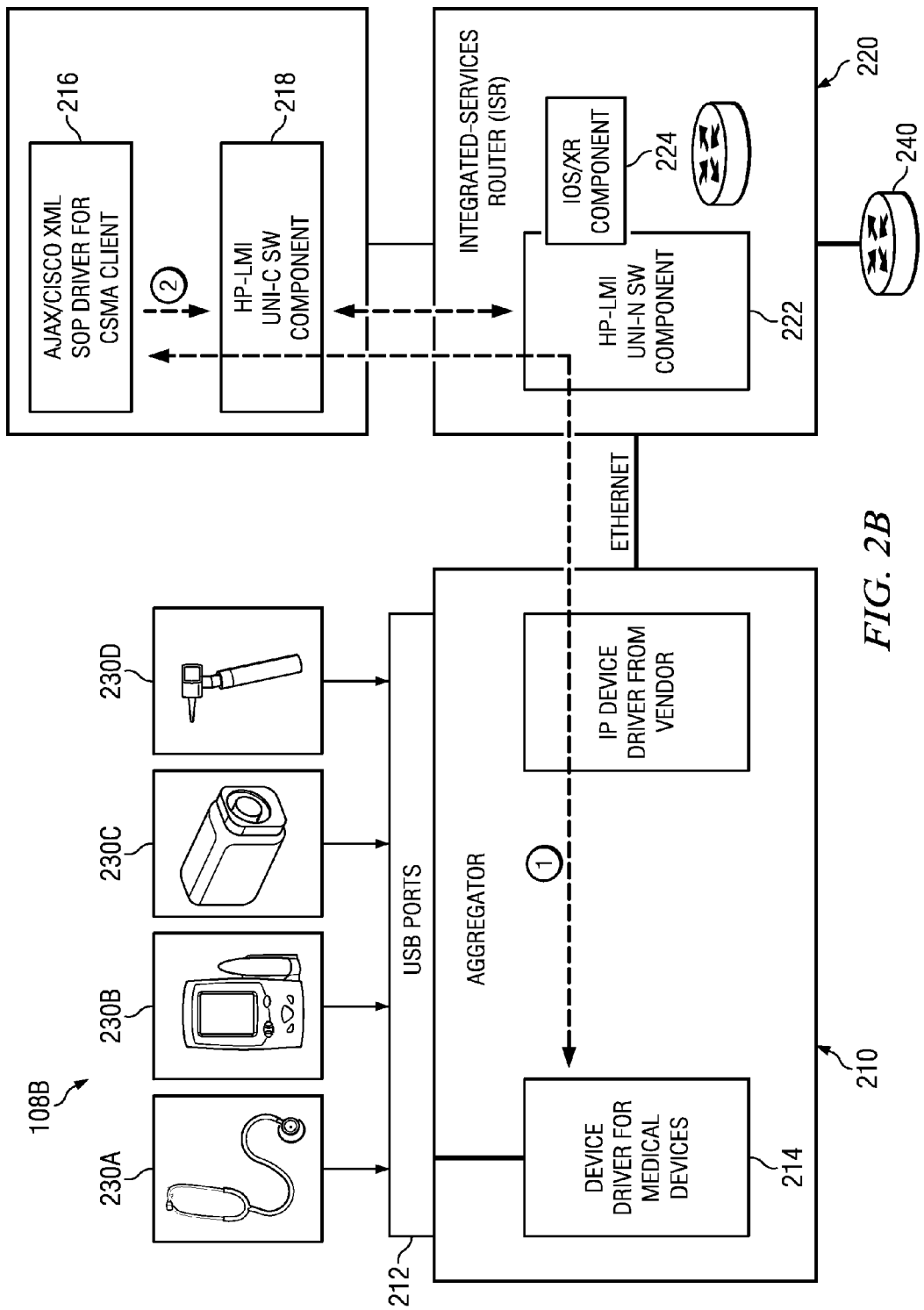

Particular embodiments may configure the components of a health-presence unit 108 differently, according to particular needs. Furthermore, within the same health presence system 100, different health-presence units 108 may be configured differently (e.g., having different types of health devices). FIGS. 2A and 2B illustrate two examples, 108A and 108B, of the health-presence unit.

In particular embodiments, health-presence unit 108A may include an aggregator 210. Aggregator 210 may be configured to manage one or more health devices, such as health devices 230, included in health-presence unit 108A. As an example and not by way of limitation, as FIG. 2A illustrates, health device 230A may be a stethoscope; health device 230B may be a blood-pressure meter; health device 230C may be a video or other camera; and health device 230D may be an otoscope. Although the present disclosure describes and illustrates particular health devices 230, the present disclosure contemplates any suitable health devices 230. In particular embodiments, aggregator 210 may have one or more ports 212, and each health device 230 may be connected to aggregator 214 through a port 212. In particular embodiments, one or more ports 212 to aggregator 210 are Universal Serial Bus (USB) ports 212. Although the present disclosure describes and illustrates particular ports 212, the present disclosure contemplates any suitable ports 212. Since not all health devices are network ready (e.g., capable of being connected to and communicate via a network), aggregator 210 in effect acts as an intermediary between health devices 230 and ultimately the network (e.g., network 102 as illustrated in FIG. 1).

In particular embodiments, aggregator 210 may include one or more device drivers (e.g., implemented as computer software) for one or more of health devices 230A, 230B, 230C, 230D. In general, a device driver may be a computer program allowing higher-level computer programs to interact with a hardware device, in this case, a health device such as health devices 230A, 230B, 230C, 230D. For example and without limitation, device drivers 214 may enable aggregator 210 to communicate with each of health devices 230A, 230B, 230C, 230D, including receiving data (e.g., medical data or device diagnostic data) from or transmitting data to health devices 230A, 230B, 230C, 230D.

In particular embodiments, aggregator 210 may include a driver 216 that enables health-presence unit 108A to communicate with a session management system (e.g., session management system 104 as illustrated in FIG. 1). Driver 216 may be implemented using any suitable protocol that corresponds to the session management system with which health-presence unit 108A communicates. For example, driver 216 may be implemented using asynchronous JavaScript and XHTML (AJAX) or service-oriented programming (SOP).

In particular embodiments, aggregator 210 may include a customer-side user network interface (UNI-C) 218. In particular embodiments, UNI-C 218 may be implemented as computer software. Health devices 230A, 230B, 230C, 230D may each use a different communication protocol. In particular embodiments, UNI-C 218 may convert the different communication protocols used by health devices 230A, 230B, 230C, 230D into a standard protocol. For example, suppose health device 230A transmits some health data (e.g., medical data generated for a patient at health-presence unit 108A) to aggregator 210 in a first communication protocol, UNI-C 218 may convert the health data from the first communication protocol to a second, standard communication protocol. In particular embodiments, aggregator 210 may monitor the current status of the health devices (e.g., health devices 230) connected to it. In particular embodiments, more specifically, UNI-C 218 may monitor the current status of the health devices connected to aggregator 210. In particular embodiments, UNI-C 218 may monitor and collect data indicating a current status of each health device 230 connected to aggregator 210 and forward the data to a network-side user network interface (UNI-N) 222, further described below. In particular embodiments, UNI-C 218 may detect when a health device 230 is connected to or disconnected from aggregator 210. UNI-C 218 thus may maintain a list of health devices 230 currently connected to aggregator 210. For example, when a new health device 230 is first connected to aggregator 210, UNI-C 218 may validate it and determine its attributes. UNI-C 218 may forward the information regarding new health device 230 to UNI-N 222 to be transmitted to a management unit 106.

In particular embodiments, UNI-C 218 may authenticate or approve the health devices 230 connected to aggregator 210, as described below with reference to FIG. 4. In particular embodiments, UNI-C 218 may manage the network bandwidth or capacity requirements as well as the quality of service desired for each of the health devices 230 connected to aggregator 210.

In particular embodiments, health-presence unit 108A may include a router 220. In particular embodiments, router 220 may be an integrated-services router (ISR). In particular embodiments, router 220 may be communicatively connected to aggregator 210 via an Ethernet connection.

In particular embodiments, router 220 may include a network-side user network interface (UNI-N) 222. Particular embodiments may implement UNI-N 222 as computer software. In particular embodiments, UNI-N 222 may communicate with UNI-C 218 and receive data (such as, for example, data indicating a current status of each of one or more health devices 230 connected to aggregator 210 or information reguarding a new health device 230 when first connected to aggregator 210) in a standard protocol from UNI-C 218 and forward the data to their intended destinations, such as another health-presence unit 108B to which health-presence unit 108A is currently connected or a management unit 106. In particular embodiments, UNI-N 222 may monitor the current status of the communication link between health-presence unit 108A and another health-presence unit (such as, for example, health-presence unit 108B). In particular embodiments, UNI-N 222 may monitor and collect data indicating the current status of the communication link between health-presence unit 108A and health-presence unit 108B and transmit the status data of the communication link to health-present unit 108B when appropriate.

In particular embodiments, UNI-N 222 may forward the information it receives from UNI-C 218 to the appropriate destinations. For example, when UNI-C 218 authenticates or approves a health device 230 connected to aggregator 210, UNI-C 218 may transmit information concerning the health device 230 to UNI-N 222. UNI-N 222, in turn, may forward the information concerning the health device 230 to a management unit 106. As another example, when UNI-N 222 receives a current status of a health device 230, such as a device problem or device failure, from UNI-C 218, UNI-N 222 may forward the device status to another health-presence unit 108B to which health-presence unit 108A is connected. As yet another example, when UNI-N 222 receives network bandwidth or capacity requirement of each of the health devices 230 or quality of services desired from UNI-C 218, UNI-N 222 may forward the request to a network decision-making engine (not shown) so that the network decision-making engine approve or disapprove the request from UNI-C 218.

In particular embodiments, router 220 may include a component 224. Particular embodiments may implement component 224 as computer software. In particular embodiments, component 224 may make decisions in the network layer for functionalities supported by router 220. In particular embodiments, component 224 may convert non-network information to network specific information.

In particular embodiments, health-presence unit 108A may include a WAN or other suitable router 240. In particular embodiments, router 240 may be communicatively connected to router 220. In particular embodiments, health-presence unit 108A may be communicatively connected to a network (network 102 as illustrated in FIG. 1) via router 240.

Health-presence unit 108B is an alternative embodiment of health-presence unit 108 and differs from health-presence unit 108A in that driver 216 and UNI-C 218 are not a part of aggregator 210 but are separate components within health-presence unit 108B. Aggregator 210 may be communicatively connected to driver 216 or UNI-C 218, and UNI-C 218 may communicate with UNI-N 222 so that health data originated from health devices 230A, 230B, 230C, and 230D, which have been processed (e.g., performing protocol conversion) and forwarded by aggregator 210, may be transmitted from UNI-C 218 to UNI-N 222 and forwarded by router 220 and router 240 to their destinations (e.g., another health-presence unit 108 connected to the network).

As illustrated in FIG. 1, one or more health-presence units 108 and one or more management units 106 may be connected to network 102. Each health-presence unit 108 may communicate directly with another health-presence unit 108 or a management unit 106. Similarly, each management unit 106 may communicate directly with a health-presence unit 108 or another management unit 106. FIG. 3 illustrates an example method for establishing a direct communication connection between two health-presence units (referred to as health-presence unit A and health-presence unit B). Note that the same concept may be used to establish a direct communication connection between a health-presence unit and a management unit or two management units.

Suppose health-presence unit A wishes to establish a direct communication with health-presence unit B. In particular embodiments, health-presence unit A may obtain network information (e.g., IP address) on health-presence unit B from a network directory service or a session management service (e.g., session management system 104 as illustrated in FIG. 1), as illustrated in step 302. Health-presence unit A may then send a communication request to health-presence unit B using the network information of health-presence unit B, as illustrated in step 304. Health-presence unit A and health-presence unit B may further exchange some handshakes (e.g., health-presence unit B sending an acknowledgement to health-presence unit A in response to the communication request).

In particular embodiments, health-presence unit B may have the option of accepting or rejecting the communication request from health-presence unit A. If health-presence unit B rejects the communication request, health-presence unit A may try to establish communication connection with healthpresence unit B again some time in the future. On the other hand, if health-presence unit B accepts the communication request, a connection (such as, for example, a peer-to-peer connection) may be established between health-presence unit A and health-presence unit B, as illustrated in step 306. Thereafter, health-presence unit A and health-presence unit B may communicate with each other directly. For example, health-presence unit A may send health data generated by the health devices contained in health-presence unit A to health-presence unit B. The health data may be associated with a patient at health-presence unit A. A doctor at health-presence unit B may review the health data and provide appropriate medical services to the patient at health-presence unit A via audio/video communication. Although the present disclosure describes and illustrates health-presence units 108 communicating with each other via a network 102, the present disclosure is not limited to health-presence units 108 communicating with each other via a network 102. As an example and not by way of limitation, two or more health-presence units 108 may communicate with each other via direct connections to each other.

Sometimes, a new health device may be connected to a health-presence unit or an existing health device may be removed from a health-presence unit. In particular embodiments, when there is a change to the health devices included in a health-presence unit, the health-presence unit or a management unit responsible for the health-presence unit may perform some configuration update.

FIG. 4 illustrates an example method for connecting a new health device to a health-presence unit. In particular embodiments, when a health-presence unit detects a new health device connected to it (e.g., a new health device is plugged into one of the USB ports of the aggregator of the health-presence unit), as illustrated in step 402, the health-presence unit may validate the new health device, as illustrated in step 404. Not all health devices may be suitable to be included in a health-presence unit. For example, a health-presence unit may require any health device connected to its aggregator to satisfy certain performance or quality requirements. Since the health data generated by these health devices are often used to diagnose health problems for patients using the health-presence unit, it may be important that all health devices included in the health-presence unit produce accurate health data, at least to a certain degree. If the new health device cannot be validated (e.g., does not satisfy the quality requirements), the health-presence unit may reject the new health device.

In particular embodiments, the health-presence unit may obtain one or more attributes of the new health device, as illustrated in step 406, such as, for example and without limitation, the type or the purpose of the health device, the communication protocol used by the health device, the network bandwidth requirement of the health device, the current condition of the health device (e.g., whether it functions correctly), or the format used to represent the data generated by the health device (e.g., the audio and video format used by the health device).

In particular embodiments, the health-presence unit may establish a communication connection with one of the management units (e.g., using the method described in connection with FIG. 3) and send the attributes of the new health device to the management unit, as illustrated in step 408. The management unit may update the information maintained on the health-presence unit to include the new health device and send configuration data for the new health device to the health-presence unit, as illustrated in 410. The health-presence unit, upon receiving the configuration data from the management unit, may configure the new health device so that it is ready for use, as illustrated in step 412.

In particular embodiments, a health-presence unit (e.g., the aggregator of the health-presence unit or more specifically, the UNI-C of the aggregator) may continuously monitor the health devices it has to ensure that all of the health devices included in the health-presence unit function correctly. This may be especially important with respect to the health data generated by the health devices. If the health-presence unit detects any abnormality or malfunction in any one of the health devices included in the health-presence unit, in particular embodiments, the health-presence unit may attempt to diagnose the errors, or report the errors to a management unit or another health-presence unit.

For example, suppose a patient at health-presence unit A is consulting with a doctor at health-presence unit B. The doctor asks the patient to measure his blood pressure using a blood-pressure meter 230B included in health-presence unit A. Further suppose that health-presence unit A detects that blood-pressure meter 230B is not calibrated correctly and that the blood pressure measured by blood-pressure meter 230B is off by 10 units. In addition to notifying the appropriate party so that blood-pressure meter 230B may be repaired, health-presence unit A may also communicate the error to health-presence unit B to be passed on to the doctor. The doctor, when making a diagnosis for the patient, may then take into consideration the faulty problem of blood-pressure meter 230B at health-presence unit A and adjust the blood pressure measurement of the patient received from health-presence unit A accordingly.

In particular embodiments, a health-presence unit (e.g., the integrated-services router of the health-presence unit) may continuously monitor the communication link it currently has with another health-presence unit or a management unit. If the health-presence unit detects any abnormality or malfunction in the communication link, it may notify the problems to the other health-presence unit currently connected to it via the communication link.

Particular embodiments may be implemented as hardware, software, or a combination of hardware and software. As an example and not by way of limitation, one or more computer systems may execute particular logic or software to perform one or more steps of one or more processes described or illustrated herein. One or more of the computer systems may be unitary or distributed, spanning multiple computer systems or multiple datacenters, where appropriate. The present disclosure contemplates any suitable computer system. In particular embodiments, performing one or more steps of one or more processes described or illustrated herein need not necessarily be limited to one or more particular geographic locations and need not necessarily have temporal limitations. As an example and not by way of limitation, one or more computer systems may carry out their functions in "real time," "offline," in "batch mode," otherwise, or in a suitable combination of the foregoing, where appropriate. One or more of the computer systems may carry out one or more portions of their functions at different times, at different locations, using different processing, where appropriate. Herein, reference to logic may encompass software, and vice versa, where appropriate. Reference to software may encompass one or more computer programs, and vice versa, where appropriate. Reference to software may encompass data, instructions, or both, and vice versa, where appropriate. Similarly, reference to data may encompass instructions, and vice versa, where appropriate.

One or more computer-readable storage media may store or otherwise embody software implementing particular embodiments. A computer-readable medium may be any medium capable of carrying, communicating, containing, holding, maintaining, propagating, retaining, storing, transmitting, transporting, or otherwise embodying software, where appropriate. A computer-readable medium may be a biological, chemical, electronic, electromagnetic, infrared, magnetic, optical, quantum, or other suitable medium or a combination of two or more such media, where appropriate. A computer-readable medium may include one or more nanometer-scale components or otherwise embody nanometer-scale design or fabrication. Example computer-readable storage media include, but are not limited to, compact discs (CDs), field-programmable gate arrays (FPGAs), floppy disks, floptical disks, hard disks, holographic storage devices, integrated circuits (ICs) (such as application-specific integrated circuits (ASICs)), magnetic tape, caches, programmable logic devices (PLDs), random-access memory (RAM) devices, read-only memory (ROM) devices, semiconductor memory devices, and other suitable computer-readable storage media.

Software implementing particular embodiments may be written in any suitable programming language (which may be procedural or object oriented) or combination of programming languages, where appropriate. Any suitable type of computer system (such as a single- or multiple-processor computer system) or systems may execute software implementing particular embodiments, where appropriate. A general-purpose computer system may execute software implementing particular embodiments, where appropriate.

Figure 5:
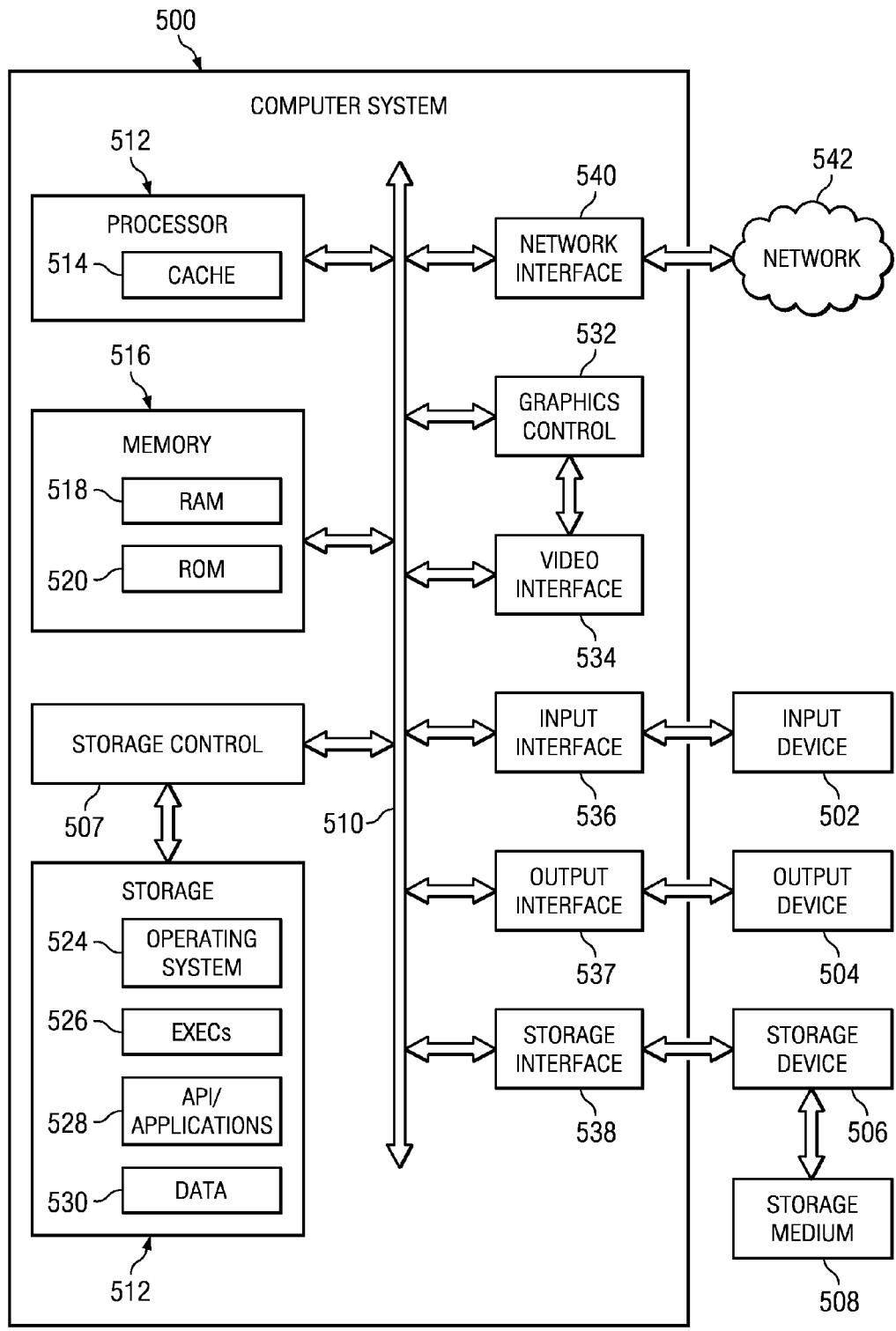
FIG. 5 illustrates an example computer system.

For example, FIG. 5 illustrates an example computer system 500 suitable for implementing one or more portions of particular embodiments. Although the present disclosure describes and illustrates a particular computer system 500 having particular components in a particular configuration, the present disclosure contemplates any suitable computer system having any suitable components in any suitable configuration. Moreover, computer system 500 may have take any suitable physical form, such as for example one or more integrated circuit (ICs), one or more printed circuit boards (PCBs), one or more handheld or other devices (such as mobile telephones or PDAs), one or more personal computers, or one or more super computers.

Computer system 500 may have one or more input devices 502 (which may include, for example, a keypad, keyboard, mouse, or stylus.), one or more output devices 504 (which may include, for example, one or more displays, one or more speakers, one or more printers.), one or more storage devices 506, and one or more storage medium 508. An input device 502 may be external or internal to computer system 500. An output device 504 may be external or internal to computer system 500. A storage device 506 may be external or internal to computer system 500. A storage medium 508 may be external or internal to computer system 500.

System bus 510 couples subsystems of computer system 500 to each other. Herein, reference to a bus encompasses one or more digital signal lines serving a common function. The present disclosure contemplates any suitable system bus 510 including any suitable bus structures (such as one or more memory buses, one or more peripheral buses, one or more a local buses, or a combination of the foregoing) having any suitable bus architectures. Example bus architectures include, but are not limited to, Industry Standard Architecture (ISA) bus, Enhanced ISA (EISA) bus, Micro Channel Architecture (MCA) bus, Video Electronics Standards Association local (VLB) bus, Peripheral Component Interconnect (PCI) bus, PCI-Express bus (PCI-X), and Accelerated Graphics Port (AGP) bus.

Computer system 500 includes one or more processors 512 (or central processing units (CPUs)). A processor 512 may contain a cache 514 for temporary local storage of instructions, data, or computer addresses. Processors 512 are coupled to one or more storage devices, including memory 516. Memory 516 may include random access memory (RAM) 518 and read-only memory (ROM) 520. Data and instructions may transfer bidirectionally between processors 512 and RAM 518. Data and instructions may transfer unidirectionally to processors 512 from ROM 520. RAM 518 and ROM 520 may include any suitable computer-readable storage media.

Computer system 500 includes fixed storage 522 coupled bi-directionally to processors 512. Fixed storage 522 may be coupled to processors 512 via storage control unit 507. Fixed storage 522 may provide additional data storage capacity and may include any suitable computer-readable storage media. Fixed storage 522 may store an operating system (OS) 524, one or more executables (EXECs) 526, one or more applications or programs 528, data 530 and the like. Fixed storage 522 is typically a secondary storage medium (such as a hard disk) that is slower than primary storage. In appropriate cases, the information stored by fixed storage 522 may be incorporated as virtual memory into memory 516.

Processors 512 may be coupled to a variety of interfaces, such as, for example, graphics control 532, video interface 534, input interface 536, output interface 537, and storage interface 538, which in turn may be respectively coupled to appropriate devices. Example input or output devices include, but are not limited to, video displays, track balls, mice, keyboards, microphones, touch-sensitive displays, transducer card readers, magnetic or paper tape readers, tablets, styli, voice or handwriting recognizers, biometrics readers, or computer systems. Network interface 540 may couple processors 512 to another computer system or to network 542. With network interface 540, processors 512 may receive or send information from or to network 542 in the course of performing steps of particular embodiments. Particular embodiments may execute solely on processors 512. Particular embodiments may execute on processors 512 and on one or more remote processors operating together.

In a network environment, where computer system 500 is connected to network 542, computer system 500 may communicate with other devices connected to network 542. Computer system 500 may communicate with network 542 via network interface 540. For example, computer system 500 may receive information (such as a request or a response from another device) from network 542 in the form of one or more incoming packets at network interface 540 and memory 516 may store the incoming packets for subsequent processing. Computer system 500 may send information (such as a request or a response to another device) to network 542 in the form of one or more outgoing packets from network interface 540, which memory 516 may store prior to being sent. Processors 512 may access an incoming or outgoing packet in memory 516 to process it, according to particular needs.

Particular embodiments involve one or more computer-storage products that include one or more computer-readable storage media that embody software for performing one or more steps of one or more processes described or illustrated herein. In particular embodiments, one or more portions of the media, the software, or both may be designed and manufactured specifically to perform one or more steps of one or more processes described or illustrated herein. In addition or as an alternative, in particular embodiments, one or more portions of the media, the software, or both may be generally available without design or manufacture specific to processes described or illustrated herein. Example computer-readable storage media include, but are not limited to, CDs (such as CD-ROMs), FPGAs, floppy disks, floptical disks, hard disks, holographic storage devices, ICs (such as ASICs), magnetic tape, caches, PLDs, RAM devices, ROM devices, semiconductor memory devices, and other suitable computer-readable storage media. In particular embodiments, software may be machine code which a compiler may generate or one or more files containing higher-level code which a computer may execute using an interpreter.

As an example and not by way of limitation, memory 516 may include one or more computer-readable storage media embodying software and computer system 500 may provide particular functionality described or illustrated herein as a result of processors 512 executing the software. Memory 516 may store and processors 512 may execute the software. Memory 516 may read the software from the computer-readable storage media in mass storage device 516 embodying the software or from one or more other sources via network interface 540. When executing the software, processors 512 may perform one or more steps of one or more processes described or illustrated herein, which may include defining one or more data structures for storage in memory 516 and modifying one or more of the data structures as directed by one or more portions the software, according to particular needs. In addition or as an alternative, computer system 500 may provide particular functionality described or illustrated herein as a result of logic hardwired or otherwise embodied in a circuit, which may operate in place of or together with software to perform one or more steps of one or more processes described or illustrated herein. The present disclosure encompasses any suitable combination of hardware and software, according to particular needs.

Although the present disclosure describes or illustrates particular operations as occurring in a particular order, the present disclosure contemplates any suitable operations occurring in any suitable order. Moreover, the present disclosure contemplates any suitable operations being repeated one or more times in any suitable order. Although the present disclosure describes or illustrates particular operations as occurring in sequence, the present disclosure contemplates any suitable operations occurring at substantially the same time, where appropriate. Any suitable operation or sequence of operations described or illustrated herein may be interrupted, suspended, or otherwise controlled by another process, such as an operating system or kernel, where appropriate. The acts may operate in an operating system environment or as stand-alone routines occupying all or a substantial part of the system processing.

The present disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend.

What is claimed is:

1. One or more non-transitory computer-readable storage media embodying software that is operable when executed to:

maintain, at a first health presence unit at a first physical location, a list of a plurality of health devices that may couple to the first health presence unit at the first physical location, the list storing a plurality of attributes associated with each health device;

monitor a first current status of a communication link coupling the first health-presence unit at the first physical location to a second health-presence unit at a second physical location remote from the first physical location for a remote health-service session, the remote health-service session comprising a health-service provider at the second physical location providing a health service to a patient at the first physical location, the first current status relating to a current capability of the communication link to communicate commands or data between the first and second health-presence units to support reliable use by the health-service provider of a particular health device of the first health-presence unit on the patient during the health-service session;

monitor a second current status of the particular health device of the first health-presence unit, the second current status relating to a current capability of the particular health device, the current capability of the particular health device comprising a condition of the particular health device and whether the particular health device is functioning correctly so as to be reliably used by the health-service provider on the patient during the health-service session;

communicate data indicating the first current status and the second current status to the second health-presence unit for presentation to the health-service provider to facilitate assessment by the health-service provider of a usefulness of the particular health device to the health-service provider during the health-service session in light of the first or second current status;

detect coupling of a new health device to the first health-presence unit;

determine, from the new health device, one or more attributes of the new health device;

store the one or more attributes of the new health device in the list of the plurality of health devices stored at the first health presence unit; and transmit the one or more attributes to a management unit data.

2. The non-transitory computer-readable storage media of claim 1, wherein the media resides at an integrated-services router of the first health-presence unit.

3. The non-transitory computer-readable storage media of claim 1, wherein the media collectively resides at an integrated-services router and a medical-device aggregator of the first health-presence unit.

4. The non-transitory computer-readable storage media of claim 1, wherein:

the health device communicates data using a first communication protocol; and the software is further operable when executed to:

convert data communicated from the health device from the first communication protocol to a second communication protocol; and communicate to the second health-presence unit for presentation to the health-service provider data from the health device using the second communication protocol.

5. The non-transitory computer-readable storage media of claim 1, wherein the software is further operable when executed to:

validate the new health device for use with the first health-presence unit based on a set of predetermined criteria;

receive from the management unit data for configuration of the new health device for use with the first health-presence unit; and configure the new health device using the data for configuration of the new health device.

6. The non-transitory computer-readable storage media of claim 1, wherein the communication link coupling the first and second health-presence units to each other is a peer-to-peer link.

7. The non-transitory computer-readable storage media of claim 6, wherein the software is further operable when executed to:
obtain from a session manager a network address of the second health-presence unit; and
establish the communication link coupling the first and second health-presence units to each other using the network address of the second health-presence unit.

8. The non-transitory computer-readable storage media of claim 1, wherein the first current status relating to the current capability of the communication link comprises information selected from the group consisting of:
a bandwidth capacity of the communications link; a quality of service of the communication link; and
an abnormality or malfunction of the communication link.

9. The non-transitory computer-readable storage media of claim 1, wherein the second current status relating to the current capability of the health device comprises information identifying a device failure.

10. A method comprising:
maintaining, by one or more computer systems of a first health presence unit at a first physical location, a list of a plurality of health devices that may couple to the first health presence unit at the first physical location, the list storing a plurality of attributes associated with each health device;
monitoring, by the one or more computer systems of the first health presence unit, a first current status of a communication link coupling the first health-presence unit at the first physical location to a second health-presence unit at a second physical location remote from the first physical location for a remote health-service session, the remote health-service session comprising a health-service provider at the second physical location providing a health service to a patient at the first physical location, the first current status relating to a current capability of the communication link to communicate commands or data between the first and second health-presence units to support reliable use by the health-service provider of a particular health device of the first health-presence unit on the patient during the health-service session;
monitoring, by the one or more computer systems, a second current status of the particular health device of the first health-presence unit, the second current status relating to a current capability of the particular health device to be reliably used by the health-service provider on the patient during the health-service session;
communicating, by the one or more computer systems, data indicating the first current status and the second current status to the second health-presence unit for presentation to the health-service provider to facilitate assessment by the health-service provider of a usefulness of the particular health device to the health-service provider during the health-service session in light of the first or second current status;
detecting a coupling of a new health device to the first health-presence unit;
determining, from the new health device, one or more attributes of the new health device;
storing the one or more attributes of the new health device in the list of the plurality of health devices stored at the first health presence unit; and
transmitting the one or more attributes to a management unit data.

11. The method of claim 10, wherein the one or more computer systems reside at an integrated-services router of the first health-presence unit.

12. The method of claim 10, wherein the one or more computer systems collectively resides at an integrated-services router and a medical-device aggregator of the first health-presence unit.

13. The method of claim 10, wherein:
the health device communicates data using a first communication protocol; and
further comprising:
converting data communicated from the health device from the first communication protocol to a second communication protocol; and
communicating to the second health-presence unit for presentation to the health-service provider data from the health device using the second communication protocol.

14. The method of claim 10, further comprising:
validating the new health device for use with the first health-presence unit based on a set of predetermined criteria;
receiving from the management unit data for configuration of the new health device for use with the first health-presence unit; and
configuring the new health device using the data for configuration of the new health device.

15. The method of claim 10, wherein the communication link coupling the first and second health-presence units to each other is a peer-to-peer link.

16. The method of claim 15, further comprising:
obtaining from a session manager a network address of the second health-presence unit; and
establishing the communication link coupling the first and second health-presence units to each other using the network address of the second health-presence unit.

17. An apparatus comprising:
a communication interface;
a memory comprising instructions executable by one or more processors; and
one or more processors coupled to the memory and operable to execute the instructions, the one or more processors being operable when executing the instructions to:
maintain, at a first health presence unit at a first physical location, a list of a plurality of health devices that may couple to the first health presence unit at the first physical location, the list storing a plurality of attributes associated with each health device;
monitor a first current status of a communication link coupling the first health-presence unit at the first physical location to a second health-presence unit at a second physical location remote from the first physical location for a remote health-service session, the remote health-service session comprising a health-service provider at the second physical location providing a health service to a patient at the first physical location, the first current status relating to a current capability of the communication link to communicate commands or data between the first and second health-presence units to support reliable use by the health-service provider of the particular health device of the first health-presence unit on the patient during the health-service session;
monitor a second current status of the particular health device of the first health-presence unit, the second current status relating to a current capability of the particular health device to be reliably used by the health-service provider on the patient during the health-service session;

communicate data indicating the first current status and the second current status to the second health-presence unit for presentation to the health-service provider to facilitate assessment by the health-service provider of a usefulness of the particular health device to the health-service provider during the health-service session in light of the first or second current status;

detect a coupling of a new health device to the first health-presence unit;

determine, from the new health device, one or more attributes of the new health device;

store the one or more attributes of the new health device in the list of the plurality of health devices stored at the first health presence unit; and transmit the one or more attributes to a management unit data.

18. The apparatus of claim 17, wherein the instructions resides at an integrated-services router of the first health-presence unit.

19. The apparatus of claim 17, wherein the instructions collectively resides at an integrated-services router and a medical-device aggregator of the first health-presence unit.

20. The apparatus of claim 17, wherein:
the health device communicates data using a first communication protocol; and
the one or more processors are further operable when executing the instructions to:
convert data communicated from the health device from the first communication protocol to a second communication protocol; and
communicate to the second health-presence unit for presentation to the health-service provider data from the health device using the second communication protocol.

21. The apparatus of claim 17, the one or more processors are further operable when executing the instructions to:
validate the new health device for use with the first health-presence unit based on a set of predetermined criteria;
receive from the management unit data for configuration of the new health device for use with the first health-presence unit; and
configure the new health device using the data for configuration of the new health device.

22. The apparatus of claim 17, wherein the communication link coupling the first and second health-presence units to each other is a peer-to-peer link.

23. The apparatus of claim 22, the one or more processors are further operable when executing the instructions to:
obtain from a session manager a network address of the second health-presence unit; and
establish the communication link coupling the first and second health-presence units to each other using the network address of the second health-presence unit.

24. A system comprising:
a first health-presence unit at a first physical location, the first health-presence unit comprising:
a first communication interface;
a first memory comprising first instructions executable by one or more first processors; and
one or more first processors coupled to the first memory and operable to execute the first instructions, the one or more first processors being operable when executing the first instructions to:

maintain, at a first health presence unit at a first physical location, a list of a plurality of health devices that may couple to the first health presence unit at the first physical location, the list storing a plurality of attributes associated with each health device;

monitor a first current status of a communication link coupling the first health-presence unit at the first physical location to a second health-presence unit at a second physical location remote from the first physical location for a remote health-service session, the remote health-service session comprising a health-service provider at the second physical location providing a health service to a patient at the first physical location, the first current status relating to a current capability of the communication link to communicate commands or data between the first and second health-presence units to support reliable use by the health-service provider of a particular health device of the first health-presence unit on the patient during the health-service session;

monitor a second current status of the particular health device of the first health-presence unit, the second current status relating to a current capability of the particular health device to be reliably used by the health-service provider on the patient during the health-service session;

communicate data indicating the first current status and the second current status to the second health-presence unit for presentation to the health-service provider to facilitate assessment by the health-service provider of a usefulness of the particular health device to the health-service provider during the health-service session in light of the first or second current status;

detect a coupling of a new health device to the first health-presence unit;

determine, from the new health device, one or more attributes of the new health device;

store the one or more attributes of the new health device in the list of the plurality of health devices stored at the first health presence unit; and transmit the one or more attributes;

the second health-presence unit at the second physical location, the second health-presence unit comprising:

a second communication interface;

a second memory comprising second instructions executable by one or more second processors; and one or more second processors coupled to the second memory and operable to execute the second instructions, the one or more second processors being operable when executing the second instructions to:

receive the data indicating the first current status and the second current status from the first health-presence unit;

receive the one or more attributes transmitted from the first health-presence unit; and display or cause to be displayed to the health-service provider the data indicating the first current status and the second current status to facilitate assessment by the health-service provider of a usefulness of the particular health device to the health-service provider during the health-service session in light of the first or second current status.

* * * * *